US012597508B2

(12) United States Patent
Ji et al.

(10) Patent No.: US 12,597,508 B2
(45) Date of Patent: Apr. 7, 2026

(54) COMPUTERIZED DECISION SUPPORT TOOL FOR POST-ACUTE CARE PATIENTS

(71) Applicant: CERNER INNOVATION, INC., Kansas City, KS (US)

(72) Inventors: Leonardo Ji, Overland Park, KS (US); Andrew Roberts, Overland Park, KS (US); Sasanka Are, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 535 days.

(21) Appl. No.: 17/024,241

(22) Filed: Sep. 17, 2020

(65) Prior Publication Data

US 2021/0082575 A1 Mar. 18, 2021

Related U.S. Application Data

(60) Provisional application No. 62/902,223, filed on Sep. 18, 2019.

(51) Int. Cl.
| | |
|---|---|
| *G16H 40/20* | (2018.01) |
| *G06N 3/044* | (2023.01) |
| *G16H 20/00* | (2018.01) |
| *G16H 50/20* | (2018.01) |

(52) U.S. Cl.
CPC ............. *G16H 40/20* (2018.01); *G06N 3/044* (2023.01); *G16H 20/00* (2018.01); *G16H 50/20* (2018.01)

(58) Field of Classification Search
CPC ........ G16H 40/20; G16H 50/20; G16H 20/00; G06N 3/044
See application file for complete search history.

(56) References Cited

U.S. PATENT DOCUMENTS

| | | | | |
|---|---|---|---|---|
| 9,336,482 | B1 * | 5/2016 | Corrado | ................. G06N 3/063 |
| 10,304,006 | B2 * | 5/2019 | Keshava | ................ G06N 20/10 |
| 10,685,747 | B1 * | 6/2020 | Wason | .................. G16H 50/30 |
| 10,825,564 | B1 * | 11/2020 | Zhang | ................. G06V 40/161 |

(Continued)

FOREIGN PATENT DOCUMENTS

WO WO-2015195836 A2 * 12/2015 ............. G16H 50/30

OTHER PUBLICATIONS

Wegiel et al., "Hospitalization Length after Myocardial Infarction: Risk-Assessment-Based Time of Hospital Discharge vs. Real Life Practice," J. Clin. Med. 2018, 7, 564; doi:10.3390/jcm7120564. (Year: 2018).*

(Continued)

*Primary Examiner* — Jonathon A. Szumny
(74) *Attorney, Agent, or Firm* — Invoke

(57) ABSTRACT

A decision support tool is provided for discharging a patient by predicting the probability of a patient's readmission based on information prior to discharge. The information used to make the prediction may include labs, vitals, diagnoses, and medications from prior encounters and from the current encounter. At least some of this information may be used to compute a readmission prediction. One or more recurrent neural networks may be utilized to generate the prediction, and one or more sequences may be generated from the patient information to feed into the one or more recurrent neural networks. Based on the prediction, one or more actions may be initiated to reduce the probability of readmission.

21 Claims, 9 Drawing Sheets

(56) References Cited

U.S. PATENT DOCUMENTS

| | | | | |
|---|---|---|---|---|
| 11,017,058 B1 * | 5/2021 | Mcdavid-Arno | ... | G06F 16/2237 |
| 11,450,419 B1 * | 9/2022 | Esman | ................... | G06F 3/0482 |
| 11,621,081 B1 * | 4/2023 | O'Keefe | ................ | G16H 50/30 |
| | | | | 705/3 |
| 2006/0112050 A1 * | 5/2006 | Miikkulainen | ........ | G16H 50/20 |
| | | | | 706/46 |
| 2007/0016441 A1 * | 1/2007 | Stroup | ................... | G16H 10/60 |
| | | | | 705/2 |
| 2011/0295622 A1 * | 12/2011 | Farooq | ................... | G16H 10/60 |
| | | | | 705/3 |
| 2011/0313788 A1 * | 12/2011 | Amland | ................. | G16H 50/20 |
| | | | | 705/3 |
| 2012/0046965 A1 * | 2/2012 | Ryan | ....................... | G16Z 99/00 |
| | | | | 705/2 |
| 2014/0372146 A1 * | 12/2014 | Kramer | ................. | G16H 50/30 |
| | | | | 705/3 |
| 2015/0081328 A1 * | 3/2015 | Tsui | ........................ | G16H 50/30 |
| | | | | 705/2 |
| 2015/0238151 A1 * | 8/2015 | Sitzman | ................. | A61B 5/363 |
| | | | | 600/483 |
| 2016/0085931 A1 * | 3/2016 | Cox | ........................ | G16H 10/60 |
| | | | | 705/3 |
| 2016/0092641 A1 * | 3/2016 | Delaney | ................. | G16H 40/20 |
| | | | | 705/3 |

| | | | | |
|---|---|---|---|---|
| 2016/0140292 A1 * | 5/2016 | Al-Dhubaib | ........... | G16H 10/60 |
| | | | | 707/748 |
| 2016/0350486 A1 * | 12/2016 | Plunkett | ................. | G16H 10/60 |
| 2017/0109494 A1 * | 4/2017 | Nunez | .................... | G16H 40/63 |
| 2017/0228507 A1 * | 8/2017 | Bottinger | .............. | G16B 40/00 |
| 2018/0096107 A1 * | 4/2018 | Demestichas | .......... | G16H 50/70 |
| 2018/0285758 A1 * | 10/2018 | Carley | ............... | G06F 16/2365 |
| 2018/0330824 A1 * | 11/2018 | Athey | .................... | G16B 40/20 |
| 2019/0034591 A1 * | 1/2019 | Mossin | ................... | G06N 3/08 |
| 2019/0283247 A1 * | 9/2019 | Chang | .................. | A61B 5/1121 |
| 2020/0082941 A1 * | 3/2020 | Wang | .................... | G16H 50/20 |
| 2020/0104412 A1 * | 4/2020 | Bart | ...................... | G06F 16/313 |
| 2020/0152333 A1 * | 5/2020 | Tomasev | ............... | G16H 70/60 |
| 2020/0342335 A1 * | 10/2020 | Burke | ................... | G16H 20/00 |
| 2020/0342955 A1 * | 10/2020 | Guo | ...................... | G16B 20/00 |
| 2021/0056413 A1 * | 2/2021 | Cheung | ................. | G16H 10/60 |

OTHER PUBLICATIONS

Barbieri et al., "Benchmarking Deep Learning Architectures for Predicting Readmission to the ICU and Describing Patients-at-Risk," arXiv:1905.08547vl (cs); Submitted on May 21, 2019. (Year: 2019).*

Jamei et al., "Predicting all-cause risk of 30-day hospital readmission using artificial neural networks," PLoS ONE 12(7): e0181173. https://doi; org/10.1371/journal.pone.0181173. (Year: 2017).*

* cited by examiner

200

210
RECEIVE PATIENT DATA FOR A PATIENT

220
GENERATE ONE OR MORE SEQUENCES

230
DETERMINE A READMISSION PREDICTION THAT A PATIENT WILL BE READMITTED INTO AN ACUTE CARE FACILITY

240
INITIATE AN ACTION BASED ON THE READMISSION PREDICTION

402

400

| NAVIGATION &(IRF OR HH) | | NAVIGATION | | IRF OR HH | | | | RED NAMES ARE <- 2 DAYS OF DC AND T.HOLD >- 80% | | | | | | |
|---|---|---|---|---|---|---|---|---|---|---|---|---|---|---|
| NAME | ACTIVE HEALTHCARE REGISTRATION | IN ECH CARE (IRF & HH) | IN IRF CARE | IN HH CARE | IRF PROJ DC DATE | IRF LO S | HH LO S | RIC | MOST RECENT PROB. | SCORE COUNT | PERSON COUNT | VISIT COUNT | MOST RECENT SCORE DTTM | READMISSION TREND |
| | | | | | | | | | | 6041 | 143 | 291 | | |
| BEN | YES | YES | NO | YES | - | - | 64 | - | 81.62% | 77 | 1 | 3 | 3/18/2019 10:30:00 | |
| SALLY | YES | YES | NO | YES | - | - | 39 | - | 61.96% | 47 | 1 | 2 | 3/18/2019 10:30:00 | |
| DAVID | YES | YES | NO | YES | - | - | 62 | - | 61.73% | 53 | 1 | 4 | 3/18/2019 10:30:00 | |
| JACK | YES | YES | NO | YES | - | - | 115 | - | 60.14% | 110 | 1 | 4 | 3/18/2019 10:30:00 | |
| DAN | YES | YES | NO | YES | - | - | 32 | - | 56.19% | 36 | 1 | 2 | 3/18/2019 10:30:00 | |
| MURPHY | YES | YES | NO | YES | - | - | 14 | - | 46.20% | 23 | 1 | 2 | 3/18/2019 10:30:00 | |

| BEN'S DATA PREDICTION MODEL: PATIENT DETAIL VIEW | | | | | | | |
|---|---|---|---|---|---|---|---|
| PACTXNDTTM | 3/18/2019 | 3/17/2019 | 3/16/2019 | 3/15/2019 | 3/14/2019 | 3/13/2019 | 3/12/2019 |
| READMISSION PROBABILITY | 84.21% | 91.68% | 82.49% | 81.28% | 84.71% | 93.54% | 85.09% |
| | | | | | | | |
| ALTERED MENTAL STATUS | YES | YES | YES | YES | YES | YES | YES |
| SHORTNESS OF BREATH | - | - | - | - | - | - | - |
| NAUSEA WITH VOMITING | - | - | - | - | - | - | - |
| CHRONIC KIDNEY DISEASE NO DIALYSIS | YES | YES | YES | YES | YES | YES | YES |
| MUSCLE WEAKNESS | - | - | - | - | - | - | - |
| CARDIAC ARRYTHMIA | - | - | - | - | - | - | - |
| MYOPATHY | - | - | - | - | - | - | - |
| HEART FAILURE | - | - | - | - | - | - | - |
| | | | | | | | |
| HEART RATE (ABNORMAL WITHIN LAST 24 HRS) | 0 | 0 | 0 | 0 | 0 | 0 | 0 |
| HEART RATE (LAST 3 DAYS VALUE HIGHER THAN BASE) | | | | | | | |
| TEMPERATURE (ABNORMAL WITHIN LAST 24 HRS) | 18 | 3 | 0 | 0 | 18 | 3 | 0 |
| PULSE OXIMETRY (LAST 3 DAYS MINIMUM) | 95 | 95 | 95 | 17 | 95 | 95 | 95 |
| RESPIRATORY RATE (LAST TWO DAYS MAX) | 20 | 20 | 20 | 20 | 20 | 20 | 18 |
| | | | | | | | |
| FUNCTIONAL MOTOR (MAX SCORE = 91.<55 HIGHER RISK) | 0 | 0 | 0 | 0 | 0 | 0 | 0 |
| BRADEN SCORE (MIN SCORE = 6. MAX SCORE = 24. <18... | 0 | 0 | 0 | 0 | 0 | 0 | 0 |
| APPETITE STATUS (CURRENT COMPARED TO INITIAL, R... | 0 | 0 | 0 | 0 | 0 | 0 | 0 |
| CHARLSON COMORBIDITY INDEX (CALCULATED BY SYS... | 0 | 0 | 0 | 0 | 0 | 0 | 0 |
| | | | | | | | |
| OPIOID MED | - | - | - | - | - | - | - |
| ANTIINFECTIVE MED | - | - | - | - | - | - | - |
| SODIUM CHLORIDE | YES | YES | YES | YES | YES | YES | YES |

COMPUTERIZED DECISION SUPPORT TOOL FOR POST-ACUTE CARE PATIENTS

CROSS-REFERENCE TO RELATED APPLICATIONS

This application claims the benefit of U.S. Provisional Application No. 62/902,223, titled "PREDICTING READMISSION OF POST-ACUTE CARE PATIENTS," filed on Sep. 18, 2019, which is hereby expressly incorporated by reference in its entirety.

BACKGROUND

Readmission of a patient to a post-acute care facility, such as a hospital, can have a wide range of effects negatively impacting a patient's health as well as effecting post-acute care facilities and service providers. For example, readmission may be associated with increased health risks, longer recovery times, and increased costs for the patient. Additionally, for post-acute care providers, readmission of a patient can result in penalties from the Centers for Medicare & Medicaid Services ("CMS") and impact fee-for-service ("FFS") payments. Further, readmission of a patient can be a quality differentiator between post-acute care providers. A study found that reduction in readmission rates is associated with an increase in operating revenues per patient for post-acute care facilities. Some studies have found 17.2% of patients, on average, are readmitted within thirty days to a post-acute care facility in the United States. Due to the impact of readmission, it is important to accurately and promptly predict readmission for post-acute care patients. Additionally, communicating the predicted readmission to a healthcare professional can help healthcare professionals reduce risk of patient readmission acute care facilities. Existing tools for predicting readmission for post-acute care patients cannot accurately predict readmission with sufficient notice before discharge to initiate actions.

SUMMARY

Systems, methods and computer-readable media are provided for implementing a decision support tool for patients receiving post-acute care based on a prediction of readmission of a patient into acute care. This prediction is made utilizing patient data recorded over time. The patient data used to make the prediction may include labs, vitals, diagnoses, medications from prior encounters and from the current encounter as well as indications of the presence of patient visits. The prediction may be available prior to discharge from a post-acute care facility or from post-acute care services. In exemplary embodiments, information that is available only at the time of discharge or after discharge may not be used. One or more sequences based on the patient data may be generated. Based on the one or more sequences, a readmission prediction may be predicted using a neural network, which may be a recurrent neural network ("RNN"). Based on the readmission prediction, one or more actions may be initiated.

BRIEF DESCRIPTION OF THE DRAWINGS

The present invention is described in detail below with reference to the attached drawing figures, wherein:

FIG. 4A depicts a graphical user interface displaying predicted readmission for a plurality of post-acute care patients, in accordance with an embodiment of the disclosure;

FIG. 4B depicts a graphical user interface displaying predicted readmission for a post-acute care patient, in accordance with an embodiment of the disclosure;

DETAILED DESCRIPTION OF THE INVENTION

Figure 1A:
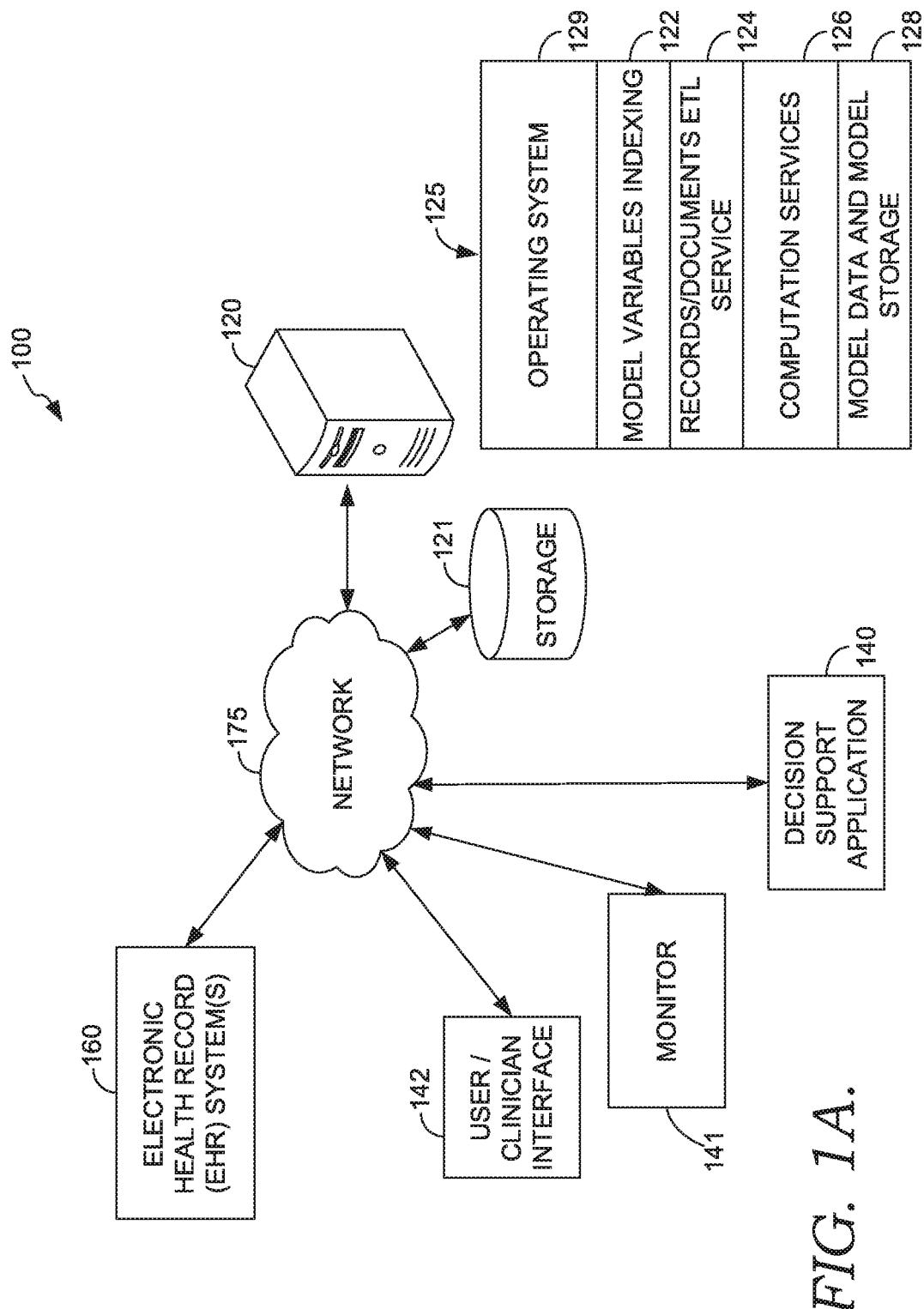
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different blocks or combinations of blocks similar to the ones described in this document, in conjunction with other present or future technologies. Moreover, although the terms "step" and/or "block" may be used herein to connote different elements of methods employed, the terms should not be interpreted as implying any particular order among or between various blocks herein disclosed unless and except when the order of individual blocks is explicitly described.

As one skilled in the art will appreciate, embodiments of the invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1A-1B.

Accordingly, at a high level, this disclosure describes, among other things, methods and systems for predicting readmission for a post-acute care patient based on patient data recorded over time. In exemplary embodiments, the readmission prediction is generated using a neural network with data received prior to discharge, such as labs, vitals, diagnoses, medications, and number of visits from prior encounters and from the current encounter. Based on the readmission prediction, one or more actions may be initiated. In some embodiments, the methods and systems may be implemented as a decision support computer application or tool for discharge planning for a patient. For instance, the readmission prediction may trigger one or more actions to reduce the likelihood of readmission, including modifying discharge instructions for the patient, scheduling additional examinations or a follow-up visit, ordering laboratory tests, or ordering one or more medications for the patient.

As previously explained, patient readmission may be associated with increased health risks, longer recovery times, and increased cost for the patient. Readmission of a patient generally can have significant consequences on a patient's health, which can be quantified through the resulting increase in healthcare costs. For example, for some types of diagnoses, the average cost of readmission was higher than the average cost of the initial admission (which may also be referred to as an index admission). Unplanned hospital readmissions account for more than $17 billion in Medicare expenditures annually according to one study. One study found there is a higher risk of mortality for patients readmitted with heart problems.

To combat the problems with readmission, it is important to accurately and promptly generate readmission predictions. However, it is difficult to predict the likelihood that a patient will be readmitted, at least partly, because a number of factors contribute to readmission to various degrees. Post-acute care patients, for example, may receive acute care services in an acute care facility (such as a hospital), be discharged into post-acute care services, which may be at an inpatient care facility or at home, and be later readmitted to an acute care facility. Many factors relating to a patient's current condition and general medical history or arising from the patient's initial acute care treatment and/or post-acute care treatment may contribute to readmission.

Some tools exist to assist in determining whether a person should be discharged. Yet, these existing tools do not account for temporal dependencies between events and tend to focus on a few of the most recent diagnoses, medications, or lab results. In other words, existing tools do not utilize a mechanism for consideration of the sequences of events and other patient data and, as such, are less accurate, especially when predicting readmission prior to discharge. In contrast to the traditional tools, the present disclosure captures sequences of events and takes the sequences into evaluation. Additionally, one existing tool that uses penalized logistic regression for predicting readmission has an area under the curve (aggregate measure of performance) of 0.79 when providing one prediction for a patient, thereby indicating a need to more accurately predict readmission at earlier points in time to decrease health risks to patients through appropriate actions. In contrast to the traditional tools, the present disclosure may predict readmission using a reverse time attention recurrent neural network model and gated recurrent units (GRUs) that, as described further in conjunction with FIG. 7, may yield an area under the curve of 0.91.

Accordingly, embodiments of the present disclosure aim to accurately predict readmission within a future time interval. This process may include predicting a likelihood of being readmitted to an acute care facility, including an acute care facility, based on patient data utilizing one or more machine learning models such as, for instance, a recurrent neural network. This patient data may include information from prior encounters and from the current encounter. As such, timely and appropriate actions can be initiated before the patient is discharged, thereby reducing the likelihood of readmission.

Specifically, embodiments include receiving patient data. This patient data received is available over time prior to patient discharge. Based on the patient data, one or more sequences may be generated. The one or more sequences may be utilized to determine a readmission prediction that a post-acute care patient will be readmitted into an acute care facility within a future time interval. Post-acute care refers to a range of medical care services that support the patient's continued recovery from illness or management of a chronic illness or disability. Post-acute care includes rehabilitation or palliative services that beneficiaries receive after a stay in an acute care facility.

In some embodiments, the future time interval may be 90 days. Predicting the readmission of a patient over the time interval of 90 days can be advantageous to preventing readmission versus shorter time intervals. The readmission prediction may be determined, for example, by inputting the one or more sequences into a recurrent neural network. Based on the readmission prediction, one or more actions may be initiated. The actions to be initiated may include displaying the readmission prediction, displaying the one or more sequences, or modifying discharge instructions for the patient. The actions, after initiated, may reduce the risk of readmission by providing resources, alerts, and information to care providers, including post-acute care providers. For example, the alert may be provided when the readmission prediction is above a threshold.

In yet another embodiment, one or more recurrent neural networks are trained to generate the readmission prediction that a patient receiving post-acute care services will be readmitted to an acute care facility within a future time interval. Accordingly, one or more sequences may be generated from patient data. In some embodiments, the patient data may be in various nomenclatures. For example, some patient data may be from post-acute care providers, acute care providers, or other healthcare facilities, and each source of the data may use different nomenclatures. In some embodiments the patient data may be standardized to a second nomenclature to generate the one or more sequences. A plurality of feature values may be determined from the patient data and used to generate the one or more sequences. At least some feature values may be arranged in chronological or reverse chronological order to form an events sequence and a visits sequence, depending on the context of the feature values. After these sequences of feature values are utilized to generate a readmission prediction, contribution scores may be determined for each feature value, which the contribution scores reflects the influence or impact on the readmission prediction.

Throughout this document, the term "readmission" may be used to refer to an episode when a patient who had been discharged from a healthcare service is admitted to the same or similar healthcare services again within a specified time interval. The healthcare service may be a service provided at any location where healthcare services may be rendered, such as an acute care facility (e.g., a hospital), a post-acute care facility, home healthcare services, or other medical care location. In some embodiments, the initial discharge and readmission are from and to a healthcare facility (e.g., an acute care facility), and further, in some embodiments, additional healthcare services may be provided to the patient in that intervening time. For example, a patient may receive acute care services at a hospital, be discharged into post-acute care, and later be readmitted to the hospital. In this case, embodiments of the disclosure described herein may predict the patient's readmission to the hospital while the patient is receiving post-acute care. In some embodiments, the prediction for readmission may be made when a patient is preparing to be discharged from post-acute care.

As used throughout this disclosure, the term "encounter" refers to a period of time in which a patient is receiving particular healthcare services. An encounter may be an office visit (e.g., an outpatient visit with a doctor or other healthcare professional), admittance into a healthcare facility or a department within a healthcare facility, or an in-home visit with a patient and a home healthcare service provider. In some embodiments, an encounter also includes a series of in-home visits between a patient and a home healthcare service provider where the series is associated with a discrete period of home healthcare services. As described herein, an encounter may be referred to as a visit.

Referring now to the drawings generally and, more specifically, referring to FIG. 1A, an aspect of an operating environment 100 is provided for practicing an embodiment of this disclosure. The operating environment 100 is merely an example of one suitable operating environment and is not intended to suggest components that are not depicted may not be used. Neither should the operating environment 100 be interpreted as having a dependency or requirement relating to a single component or combination of components illustrated therein. Similarly, although some items are depicted in the singular form, plural items are contemplated as well (e.g., what is shown as one data store might really be multiple data-stores distributed across multiple locations); however, showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for example, predicting patient readmission, include readmission for post-acute care patients. Operating environment 100 includes one or more electronic health record (EHR) systems, such as hospital EHR system 160, communicatively coupled to network 175, which is communicatively coupled to computer system 120. In some embodiments, components of operating environment 100 that are shown as distinct components may be embodied as part of or within other components of operating environment 100. For example, EHR system 160 may comprise one or more EHR systems, such as hospital EHR systems, health information exchange EHR systems, ambulatory clinic EHR systems, and/or psychiatry/neurology EHR systems. Such EHR systems 160 may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network 175. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although operating environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a web-based application or applet. A healthcare provider application may facilitate accessing and receiving information from a user or healthcare provider about a specific patient or set of patients for which the likelihood of being readmitted is predicted according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined readmission prediction and/or issuing an alert) described herein; or other health-related information, and facilitates the display of results, recommendations, or orders, for example. In an embodiment, user/clinician interface 142 also facilitates receiving orders, such as orders for more resources, from a user based on the results of predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient, a set of patients, or a population according to the embodiments presented herein. Such information may include historical data; health care resource data; variables measurements, time series, and predictions (including plotting or displaying the determined outcome and/or issuing an alert) described herein; or other health-related information. Application 140 and/or interface 142 also facilitates the display of results, recommendations, or orders, for example. In an embodiment, application 140 also facilitates receiving orders, scheduling time with care providers (including follow-up visits), or queries from a user, based on the results of the patient readmission prediction, which may utilize user interface 142 in some embodiments.

Decision support application 140 may also be used for providing diagnostic services or evaluation of the performance of various embodiments. As shown in example environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment, monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. It is also contemplated that the clinical or physiological information about a patient or population of patients, such as the monitored variables, patient demographics, patient history, and/or clinical narratives regarding the patient, used according to the embodiment of the invention disclosed herein may be received from a patient's historical data in EHR system 160, or from human measurements, human observations, or automatically determined by sensors in proximity to the patient.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting application 140 for performing signal conditioning of a measured patient variable. In one embodiment, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting acute care readmission for a patient who has received post-acute care services based on patient data for a plurality of dates to reduce the risk of readmission as described in connection to method 200.

Computation services 126 perform statistical software operations. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing performing sequential modeling using one or more models, including decision trees and logistic models, for predicting a readmission, such as the models described in connection to FIGS. 2-6.

In some embodiments, stack 125 includes file system or cloud-services 128. Some embodiments of file system/ cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y," for example), and itemsets index information; association rulebases; agent libraries, solvers and solver libraries, and other similar information including data and computer-usable instructions; patient-derived data; and healthcare provider information, for example.

In some embodiments, storage 121 includes training data for training one or more machine learning models, including one or more models for generating a prediction of readmission for a post-acute care patient. In exemplary embodiments, one or more neural networks (e.g., a recurrent neural network) is utilized to predict readmission. However, reference to a recurrent neural network is not intended to be limiting. For example, and without limitation, the one or more machine learning models may include any type of machine learning model, such as a machine learning model using linear regression, logistic regression, decision trees, support vector machines (SVM), Naïve Bayes, k-nearest neighbor (KNN), K means clustering, random forest, dimensionality reduction algorithms, gradient boosting algorithms, neural networks (e.g., auto-encoders, convolutional, recurrent, perceptrons, Long/Short Term Memory (LSTM), Hopfield, Boltzmann, deep belief, deconvolutional, generative adversarial, liquid state machine, etc.), and/or other types of machine learning models.

Additionally, it is contemplated that the term "data" used herein includes any information that can be stored in a computer storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
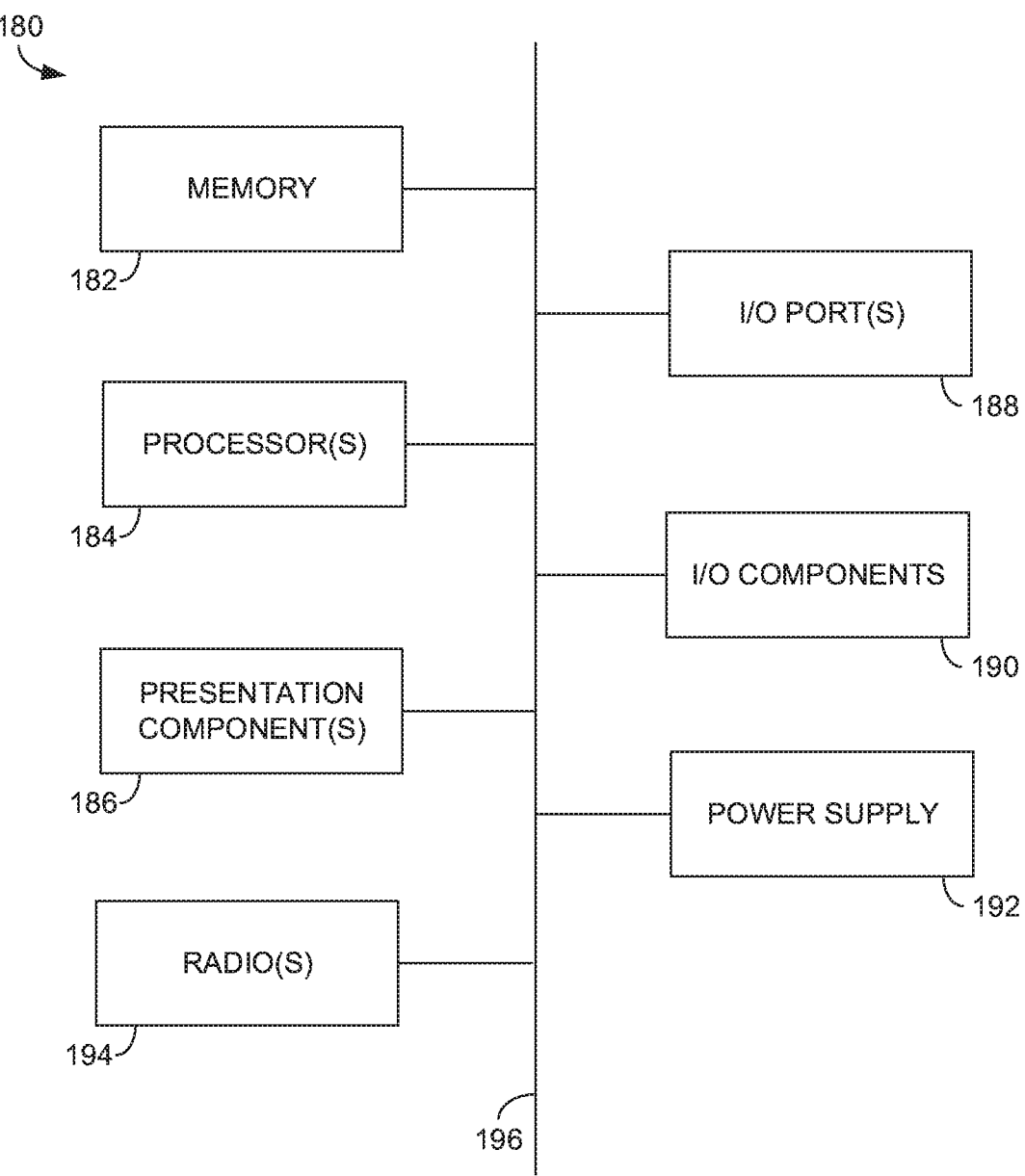

Turning briefly to FIG. 1B, there is shown one example embodiment of computing system 180 representative of a system architecture that is suitable for computer systems such as computer system 120. Computing system 180 includes a bus 196 that directly or indirectly couples the following devices: memory 182, one or more processors 184, one or more presentation components 186, input/output (I/O) ports 188, I/O components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 180 comprises radio(s) 194 that facilitates communication with a wireless-telecommunications network. Illustrative wireless telecommunications technologies include CDMA, GPRS, TDMA, GSM, and the like. Radio(s) 194 may additionally or alternatively facilitate other types of wireless communications including Wi-Fi, WiMAX, LTE, or other VoIP communications. As can be appreciated, in various embodiments, radio(s) 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
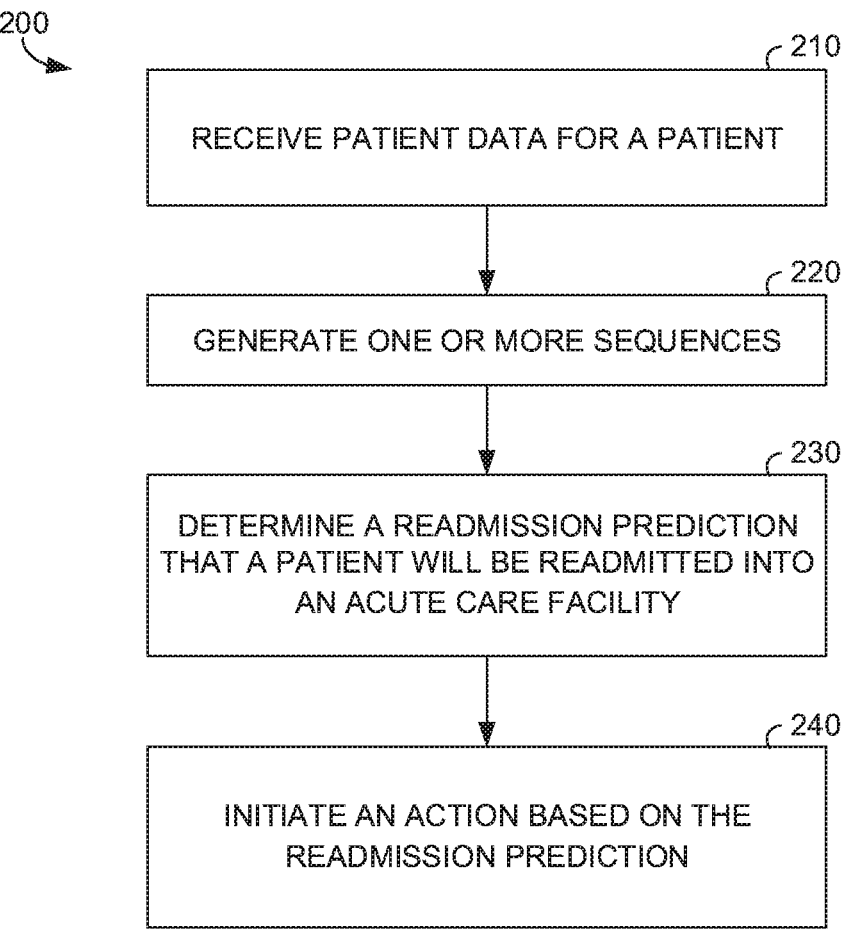
FIG. 2 depicts a flow diagram of a method for predicting readmission for a post-acute care patient, in accordance with an embodiment of the disclosure.

Turning now to FIG. 2, an example embodiment of a method for predicting readmission for a post-acute care patient is provided and is referred to generally as method 200. Method 200 may be performed by one or more components of environment 100, such as decision support application 140. Each block or step of method 200 comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a stand-alone application, a service or a hosted service (stand-alone or in combination with another hosted service), or a plug-in to another product, to name a few.

In particular, example method 200 utilizes one or more machine learning models, such as recurrent neural network, with patient data that is available prior to discharge to predict a readmission prediction that the patient will be readmitted within a future time interval and provide one or more actions to the readmission prediction. In some embodiments, method 200 is suitable for implementation as a computer-performed decision support tool or application for providing care to patients or discharge planning for patients based on the readmission prediction that is more accurate than conventional technology would otherwise allow.

In accordance with method 200, at block 210, patient data is received for a patient. In some aspects, the patient is an individual receiving post-acute care services, which may include inpatient, outpatient, and/or home healthcare services. The patient data may comprise current patient data, and/or historical patient data. In exemplary aspects, current patient data includes data relating to the patient's labs, vitals, diagnoses, medications from prior encounters and from the current encounter (e.g., the current admission to a healthcare facility, current visit to an outpatient facility, or current period of receiving home healthcare services). The current encounter information may include a diagnosis and/or treatment (including medications administered or ordered and procedures performed or ordered). During the current encounter, the patient may be diagnosed or treated with a condition such as asthma, cancer, or heart disease, for example. Current patient data may further include lab results (e.g., physiological data), including vital sign data, from the current encounter. The patient data may also indicate the existence of patient visits, including the type of patient visits (e.g., inpatient stay, doctor visit). The patient data may also indicate a number of visits or be used to determine a number of visits.

In some embodiments, patient data may include patient demographic data. Patient demographics may include age, sex, race, nationality, socioeconomic status, marital status, and/or employment status. This data may further include the patient's insurance information, such as the insurance provider and the type of plan. In some embodiments, patient demographic information is not directly used to generate a prediction of readmission. In these cases, patient demographic information is not input into the machine learning predictor, such as the recurrent neural network described with respect to FIG. 3. Further, historical patient data may include the patient's medical history and/or family history. Historical patient data may also include information about the patient's past encounters at the current healthcare facility, post-acute care facility, or other facilities. In some embodiments, historical patient data includes previous diagnoses, medications, and lab results.

This patient information may be received from different sources. For instance, in one embodiment, all patient data is received at block 210 from the patient's EMR. In other embodiments, data relating to the patient's current condition and/or patient demographics may be received directly from a user, such as the patient or a care provider, inputting such information into a user device. Some current patient data, such as patient variable values, may be received from one or more sensors or monitoring devices or directly from a laboratory running the laboratory procedures. Additionally, historical patient information may be received from the patient's EMR and/or from insurance claims data for the patient. For example, EMR data from in-home care services, hospitals, or any healthcare facility may be received. In an alternative embodiment, the patient's history may be received directly from the patient, such as during registration when admitted to a care facility for the current encounter or starting the current care services (such as with in-home care services).

At block 220, method 200 includes generating one or more sequences based on the patient data recorded over time. Some embodiments may include at least two sequences. In exemplary embodiments, the sequences are sequences of feature values determined from the patient data. In one embodiment, patient data from which feature values are determined may include dialysis features, inpatient medications, prescribed medications, and documentation. The sequences, in some embodiments, are organized across time in chronological order. For instance, a sequence may be a sequence of the patient's values for select features arranged over time. In some embodiments, determined feature values are arranged in reverse chronological order. In embodiments with at least two sequences, one may be arranged in chronological order and the other may be arranged in reverse chronological order.

A sequence may be created using time and/or date information associated with a feature within the patient data and appending the feature values together based on the time and/or date information. For instance, date/time stamp may be automatically associated with patient data as it is received (e.g., in the patient's EMR). Additionally or alternatively, a date and/or time may be associated (automatically or manually) with the patient data according to the date and/or time of the encounter from which the information arose. For instance, billing or insurance claims data may identify diagnoses, procedures, medications, and labs for a particular encounter (e.g., visit or inpatient stay) may be automatically associated with the date for the visit or stay. Based on the associated date and/or time information, the features may be arranged. In some instances, each sequence is arranged in a chronological order. Alternatively, a sequence may be arranged in reverse chronological order.

In exemplary embodiments, generating one or more sequences includes generating an events sequence and generating a visits sequence for the patient. An events sequence, as used herein, arranges feature values for events. An event may include a lab result, a diagnoses, a medication (ordered or administered), and a procedure (ordered or performed). For example, a patient may have testing performed, receive a diagnoses based on the testing, and be prescribed a medication for the diagnosed condition. In this example, an events sequence arranged in chronological order may include lab results (first event), diagnoses (second event), and medication ordered (third event). A visits sequence, as used herein, arranges the presence of visits (or encounters). For example, a patient may have a first visit with a primary care physician, a second visit to the emergency department, and a third visit with a cardiology specialist. In this example, a visits sequence arranged in chronological order may include a primary care visit, an emergency department visit, and a specialist visit. The feature values used for the events sequence may come from at least some visits during the visits sequence. For instance, considering the example events sequence described above, the lab results (first event) may occur within the first visit while the diagnoses and the medication may occur during the second or third visit.

Generating an events sequence and generating a visits sequence may each include transforming the received patient data into a format that is useable for creating the respective sequence. As such, feature values may be generated from the patient data. Each feature (e.g., lab results, medications, procedures, diagnoses, visits) may include one or more feature-specific values within the received patient data (e.g., 150 mmHg/90 mmHg for blood pressure lab result or acebutolol for medication), and method 200 may include determining new values to use in generating the sequences. In addition, in some embodiments, the feature values may be determined using a reference range specific to a patient, the reference range comprising normal values and abnormal values (or high and average, or low and average), for example. Further, in some embodiments, if a patient-specific reference range is not stored in the patient's EMR, a default reference range determined for a larger population may be utilized for determining the feature values.

The determined value may be a risk level or category or, in some instances, may be in a binary format (e.g., yes or no; present or not present). In some embodiments, determining a feature value that represents a risk level for each feature includes identifying the feature-specific values within the patient data as having a positive influence, a negative influence, or a neutral influence on the patient's health. Although feature values are described as positive, negative, or neutral, this is intended to be non-limiting. In some embodiments, a determined feature value is one of "high risk," "neutral," or "low risk." In other embodiments, the determined feature value is one of "low risk," "low-neutral risk," "neutral risk," "high-neutral risk" and "high risk." Determining the new feature value (e.g., risk level) may include comparing the feature-specific value to a threshold value or threshold range of values. In some embodiments, this threshold information is stored in a reference database.

Further, the determined feature values may be based on the type of feature and/or the type of sequence for which the feature value is generated. For example, visit indicators in patient data may be used to generate feature values corresponding to a type of visit. A type of visit may include, for example and without limitation, a physician visit, an inpatient stay, or an outpatient procedure. In some embodiments, a visit may indicate whether a physician visit is with a primary care physician or a specialist. In some embodiments, a feature value for a visit is a binary value (e.g., yes, no) indicating whether a particular type of visit is present within a particular time frame.

In some embodiments, patient data is received from different sources and, as such, may be provided in different nomenclatures. For example, a first diagnosis from a first healthcare service provider may use one nomenclature while a second diagnosis from a second healthcare service provider may use a different nomenclature. To facilitate integrating data from different sources into a single sequence and inputting the sequence into a predictor model, generating a sequence may include determining feature values in a standard (or common) nomenclature. This process may be done by mapping features in different nomenclatures to a standard nomenclature. For instance, for diagnoses, a mapping scheme may be used to map different diagnostic codes that relate to the same diagnoses to a common nomenclature. This mapping helps enable deployment of this technology across multiple entities, such as healthcare facilities and systems, that may utilize different nomenclatures. Further, some embodiment may employ an ontology to allow grouping of multiple concepts into one. For example, many medications may have different brand or generic names and, in some instances, dosage units, and an ontology mapping scheme may be used to map those different medications names (or dosage units) in EHRs to a single "drug classification" concept. Such grouping using an ontology reduces the length of an sequence for processing by the machine learning mechanism, such as an RNN, which may lead to faster and most efficient model training and execution.

Although normalizing patient data (via putting the data into a standard nomenclature and/or determining feature values) is described above as occurring before the sequence is generated, it is understood that, in some embodiments, the sequence may be generated before or simultaneously with normalizing the patient data.

At block 230, a likelihood that a post-acute care patient will be readmitted to an acute care facility (which may also be referred to as the readmission prediction) is computed based on the one or more sequences. The readmission prediction comprises a likelihood the patient will be readmitted to an acute care facility within a particular future time interval. In exemplary embodiments, the future time interval is 90 days such that it is predicted whether the patient will be readmitted to an acute care facility at some point within 90 days from the time the prediction is generated.

In exemplary aspects, the prediction of readmission is made prior to the time of discharge from the current healthcare services. For instance, in some embodiments, the prediction is made up to three days prior to discharge. As such, the patient information that is used to predict the readmission prediction is information that is only available prior to discharge. In other words, information that becomes available at the time of discharge for the current healthcare services or after may not be used.

As stated, in exemplary embodiments, a recurrent neural network (RNN) is utilized to predict the patient's likelihood of being readmitted to an acute care facility within the future time interval. A neural network includes layers of connected nodes. In an exemplary recurrent neural network, connections between nodes form a temporal sequence such that a recurrent neural network can use internal memory to process sequential inputs. Utilizing sequential inputs provides a better understanding of the context of certain patient information and, as such, is advantageous in yielding a more accurate prediction of readmission due to high sensitivity, high precision, and a low production of false positives that divert resources to patients who do not need those resources.

Figure 3:
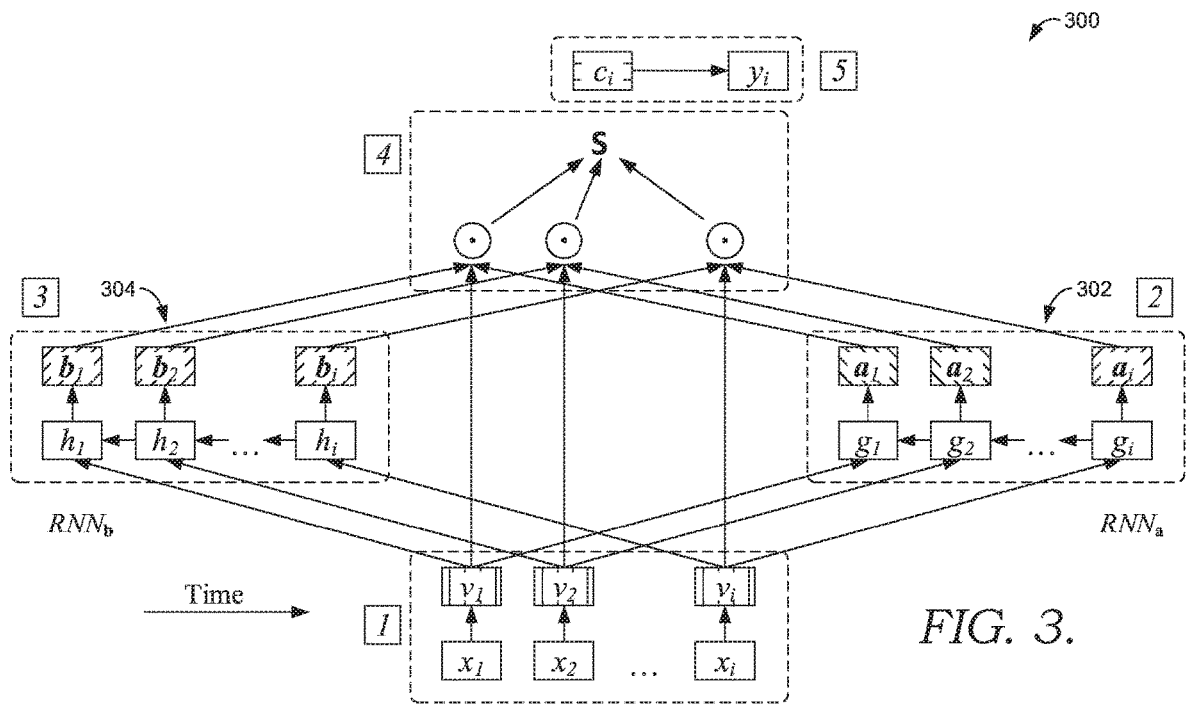
FIG. 3 depicts a schematic representation of a reverse attention RNN architecture, in accordance with an embodiment of the present disclosure.

FIG. 3 depicts an exemplary schematic representation of a reverse attention RNN architecture 300 that may be utilized for generating the readmission prediction in embodiments of method 200 in FIG. 2. In some embodiments, the RNN architecture 300 comprises cyclical connections between nodes or units of a network, wherein the cyclical connections may be trained for sequence learning. As illustrated in FIG. 3, embodiments of the RNN architecture 300 may implement two GRU layers (an event layer 302 and a visit layer 304). A connection from a neuron in the visit layer 304 to a neuron in event layer 302 is a feedback (or top-down) connection. Additionally, the cyclical connections may be fully connected or locally connected. Fully connected networks have a neuron in one layer that may communicate output to each neuron in the other layer, so that each neuron in the other layer will receive input from each neuron in the one layer. Alternatively, in the locally connected network, a neuron in the visit layer 304 may be connected to a limited number of neurons in the event layer 302.

The reverse attention RNN architecture 300 may be trained at a faster rate than traditional tools. For example, in some embodiments, the reverse attention RNN architecture 300 may be trained using an optimizer, such as an Adam Optimizer. Additionally, the reverse attention RNN architecture 300 may be retrained at a later point in time from an initial training. Reverse attention permits attention vectors to dynamically change at each step. In one non-limiting example, the reverse attention RNN architecture 300 may be trained using millions of rows of data from results, medications, and conditions of many patients for determining feature values.

Further, each GRU layer may be used, at least in part, to generate the readmission prediction and may execute the one or more sequences in a reverse chronological order. In the example shown in FIG. 3, the visit layer 304 may receive an input of a visits sequence in reverse chronological order, and the event layer 302 may receive an input of an events sequence in chronological order. Input into the visit layer 304 may include a visits sequence for the patient and, as such, includes patient information related to the number and frequency of visits (e.g., number of encounters) of the patient to a healthcare facility. Input into the event layer 302, on the other hand, may include an events sequence for the patient and, as such, may include patient information related to diagnoses, medications, lab results, and procedures from patient encounters or visits. Additionally, each of the event layer 302 and the visit layer 304 may be associated with a bias value (also referred to as weight), which may be manually input or adjusted dynamically. For example, a bias value may be given to each node in a layer. The layer's bias value may impact the relative value of the layer when determining the readmission prediction. A bias value may be applied at various inputs at nodes in the network. As the network learns, the weight or bias value may be stored in arcs and nodes in terms of node biases and arc weights. In addition, training data may be used to for predicting a set of bias values.

Different activation functions may be utilized for the visit layer 304 and the event layer 302. In exemplary embodiments, the visit layer 304 utilizes a hyperbolic tangent function, and the event layer 302 utilizes a softmax function. Utilizing these different activation embodiments may harmonize the fact that two layers have different biases. The visit layer 304, for instance, may be associated with a positive bias value because any visit may generally be associated with a health issue and, therefore, indicate a risk of readmission increasing. On the other hand, in addition to positive values indicating a health risk, the event layer 302 may have negative values because event features may not always be indicate a risk (e.g., lab results may indicate good health).

As shown in the schematic representation of FIG. 3 and as discussed herein, the neural network may utilize the following functions to generate the prediction:

$$g_i, g_{i-1}, \ldots, g_1 = RNN_\alpha(v_i, v_{i-1}, \ldots, v_1),$$

$$e_j = w_\alpha^\top g_j + b_\alpha, \text{ for } j = 1, \ldots, i$$

$$\alpha_1, \alpha_2, \ldots, \alpha_i = \text{Softmax}(e_1, e_2, \ldots, e_i)$$

$$h_i, h_{i-1}, \ldots, h_1 = RNN_\beta(v_i, v_{i-1}, \ldots, v_1)$$

$$\beta_j = \tanh(W_\beta h_j + b_\beta), \text{ for } j = 1, \ldots, i,$$

Further, in some embodiments, a cross-entropy loss function may be used to calculate error and further tune the RNN. As such, the error may be calculated by the following:

$$H_p(q) = -\frac{1}{N} \sum_{i=1}^{N} y_i \cdot \log(p(y_i)) + (1 - y_i) \cdot \log(1 - p(y_i))$$

In some embodiments an RNN may not be implemented, but rather, a different type of neural network, such as a convolution neural network, may be implemented with the one or more sequences as input.

Returning to block 230 of FIG. 2, the generated prediction may be in the form of a percentage, with values closer to 1 indicating a higher likelihood of readmission. A score (such as a numerical or categorical score) may be assigned to the patient based on the predicted likelihood. For example, a prediction likelihood of 0.8 may result in the patient being assigned to a "high risk" score.

In addition to generating the prediction, method 200 may also include identification contributions of one or more features. The contributions reflect the impact of a feature value on the predicted readmission risk. For example, higher contribution scores may be assigned to feature values that had a greater influence in the RNN determining the patient's risk of readmission. These contributions may be determined using a softmax function in some aspects. In some embodiments, the contributions may be presented with the predicted likelihood to a user. Because clinicians exercise their own clinical judgments in treating patients, providing the contributions supporting a patient's predicted readmission risk facilitates a clinician being able to use his or her own judgment in accepting or rejecting the predicted likelihood and any resulting actions to be initiated. In some embodiments, this information (a predicted risk and supporting contribution scores) is stored in JSON format and can be integrated into third-party applications with a web service. Additionally, the data may be used to create graphical user interfaces for presenting the information to the user in JSON or other format.

Returning to method 200 of FIG. 2, at block 240, one or more actions may be initiated based on the readmission prediction. The actions may be actions to mitigate or reduce the risk of the patient being readmitted. In some embodiments, an action to initiate may include emitting or otherwise electronically communicating a recommendation or notification to a caregiver responsible for the patient's care, such as a physician or nurse. This notification may be presented via a user/clinician interface (such as interface 142 described in FIG. 1A). The notification may indicate the readmission prediction of the patient being readmitted within the future time interval, the notification may include the one or more sequences, and/or present instructions to not discharge the patient or to discharge the patient with particular discharge instructions. Additionally, some embodiments of block 230 may further include storing the result of the readmission prediction in an EHR associated with the patient and further may include providing the patient's EHR (or facilitating access to the EHR) in the notification.

In example embodiments, an action to initiate may include modifying the patient's discharge protocol to one that is designed to reduce the likelihood of readmission. The modified discharge protocol may include requiring additional approval of discharge by a care provider (which may require further examination by a care provider), providing discharge instructions tailored to reduce the risk of readmission, scheduling a follow-up appointment with a care provider within a specified time from discharge, ordering additional testing, and prescribing medications designed to reduce the risk of readmission. As such, the action may include scheduling a time for a care provider to see the patient prior to discharge or scheduling a follow-up appointment within a designated time period that is less than the time period (e.g., 30 days) for which the readmission prediction is forecasted. The action may also include electronically adding one or more documents with special discharge instructions to a queue associated with the patient's record, which may include a queue designating documents for printing and/or providing to the patient. One or more care providers, such as a discharge nurse, may be notified of the additional documentation. Further, additional testing to confirm the increased risk and medications may be ordered prior to patient's discharge.

One or more of these actions may be performed by automatically modifying computer code executed in a healthcare software program for treating the patient and/or discharging planning, thereby transforming the program at runtime. For example in one embodiment, the modification comprises modifying (or generating new) computer instructions to be executed at runtime in the program, the modification may correspond to a change in a discharge procedure due to the predicted readmission.

In some embodiments, the actions may be initiated automatically when the probability of readmission satisfies a threshold level (i.e., a threshold probability). In some embodiments, the threshold probability may be a value within a range of 0 to 1. In some embodiments, the threshold probability is between 0.5 and 1. For example, in one embodiment, the threshold probability may be 0.75.

In some embodiments, the threshold may customizable for a particular clinician or healthcare provider and may be configured by a software application that is separate from but works in conjunction with the software application running the predictive model. Selections for thresholds may include a selection for risk categories, which may each be associated with an action or set of actions. In one embodiment, threshold configurations may include a threshold selection for very high risk, a threshold selection for high risk, a threshold selection for low risk. Additionally, a threshold may be configured based on risk level relative to other patients. For example, a user, such as a clinician or representative of healthcare facility, may select very high risk for a top 10% of patients, high risk for the following 15% of patients, and low risk for the following 75% of patients. In embodiments in which threshold is based on relative risk, thresholds may be configured differently depending on the statistical method used (e.g. a maximum absolute value of a true positive rate minus a false positive rate, or optimal point on an ROC curve).

Further, the threshold level may vary depending on the action. For instance, a threshold probability may be set for providing additional discharge instructions such that, when the threshold is satisfied, an action for providing additional discharge instructions is automatically initiated. A different threshold, such as a higher probability, may be set for initiating an exam by a care provider to approve discharge or for ordering additional testing. In some embodiments, a lower threshold value, such as 0.3 or 0.4, may be utilized for ordering continued monitoring of the individual. As used herein, satisfying a threshold may refer to meeting or exceeding a threshold value.

FIGS. 4A and 4B depict example screenshots from a computing device, showing aspects of an example graphical user interface (GUI) for a computer software application or app. The GUI depicted in the screenshots in FIGS. 4A and 4B may be examples of user/clinician interface 142 in FIG. 1A and may be for a computer decision support application, such as decision support application 140 described in FIG. 1A. The computer decision support applications of the GUI may be operating on (and GUIs may be displayed on) a user computer device 402, which may be embodied as computer system 120 in FIG. 1.

FIG. 4A, specifically, depicts GUI 400 graphical user interface 400 displaying predicted readmission scores for a plurality of post-acute care patients, which are represented by patient identifier in patient identifier column 408 of GUI 400. The readmission predictions may be in the form of a most recently calculated probability of readmission display in readmission prediction column 404. The readmission prediction column 404 may include readmission predictions displayed as a probability score in percentages, but it is contemplated that other numerical, alphabetical, or alpha-numerical score may be generated to display the prediction likelihood. In some embodiments, the probability score over a period of time may be stored in a database, and displayed over time as a readmission trend line, as such in trend column 410 in GUI 400. The trend line represents a change (or lack thereof) over a period of time in a patient's risk (or likelihood) of readmission. The readmission trend lines are often useful interface elements to provide user clinicians with information about patient risks and indictors of when to intervene when a patient's risk deteriorates. A visit column 406 in GUI 400 may be included to indicator the number of visits for each of the plurality of patients 408. Additional details regarding generating a readmission prediction score are discussed with respect to method 200 of FIG. 2.

FIG. 4B depicts a graphical user interface 430 displaying predicted readmission likelihoods for a particular post-acute care patient. For example, and with reference to FIG. 4A, a user may select a particular patient (e.g., "Ben") from the patient identifier column 408 of GUI 400 in FIG. 4A to view GUI 430 describing additional information about the patient. This additional information in GUI 430 may include a history of readmission probabilities computed for the patient as shown in readmission probability row 432 as well as feature values from the patient data that are utilized in computing the readmission probability. Continuing with FIG. 4B, GUI 430 may further include indicators 434 and 436 to highlight high risk and/or low risk attributes of the patient data. The indicators 434 and 436 may visually represent which items of patient data are associated with higher risks of readmission (e.g., indicator 436) and lower risk of readmission (e.g., indicator 434). These indicators may be generated based on contribution scores for the features in the patient data. Additional details regarding generating a readmission prediction and the contribution values are discussed with respect to method 200 of FIG. 2.

Figure 5:
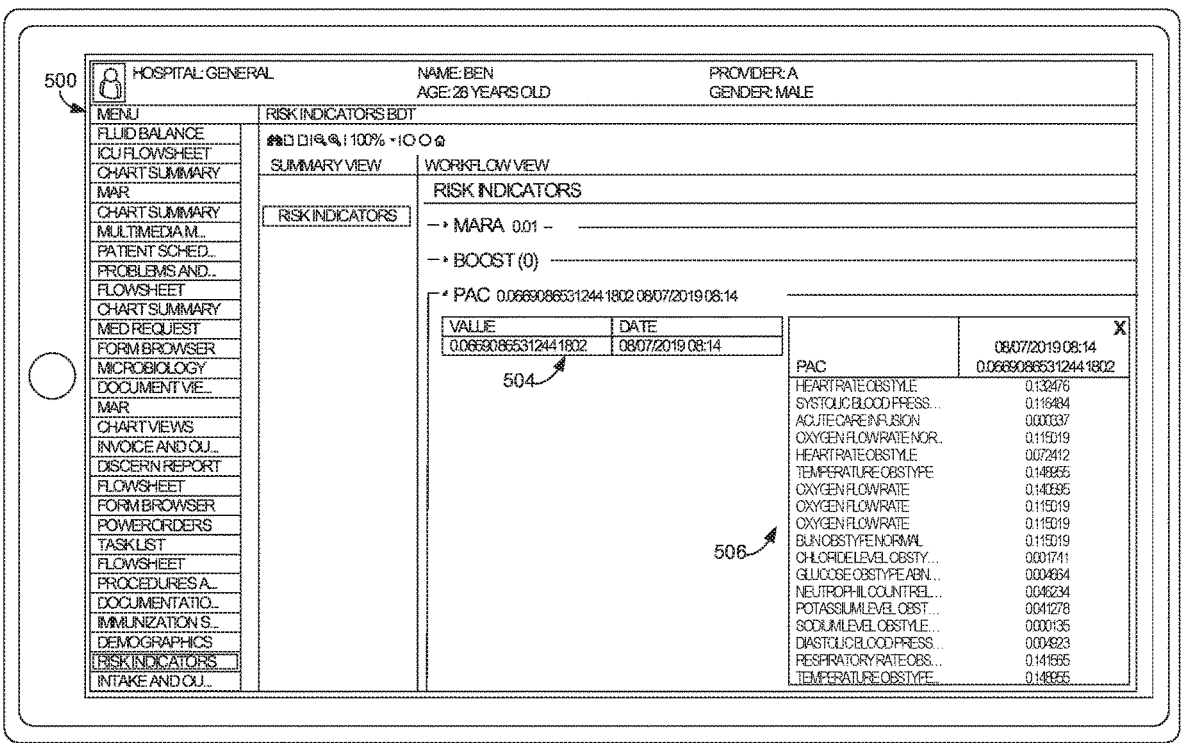
FIG. 5 depicts a graphical user interface displaying contribution scores of patient data for predicting readmission for a post-acute care patient, in accordance with embodiments of the disclosure.

FIG. 5 depict an example screenshot from a computing device, showing aspects of an example graphical user interface (GUI) 500 for a computer software application or app. The GUI 500 may be examples of user/clinician interface 142 in FIG. 1A and may be for a computer decision support application, such as decision support application 140 described in FIG. 1A. The computer decision support applications of the GUI 500 may be operating on (and GUI 500 may be displayed on) a user computer device 502, which may be embodied as computer system 120 in FIG. 1.

Specifically, GUI 500 of FIG. 5 shows a readmission prediction for a patient within a patient's healthcare record. GUI 500 identifies the readmission probability and the date and time the probability was computed, as shown in table 504. GUI 500 further provides contributions of patient health data utilized for predicting readmission. For example, table 506 of GUI 500 lists various features for which feature values were extracted from patient data and utilized to predict the readmission probability in table 504. For each feature, table 506 further includes a contribution score, indicating a relative amount to which the particular feature impacted the readmission prediction. As such, for a particular patient, a user, such as a care provider may, use GUI 500 to identify the contribution scores for various features that resulted in a particular readmission prediction on a particular date. Additional details regarding generating a readmission prediction and the contribution values are discussed with respect to method 200 of FIG. 2.

Figure 6:
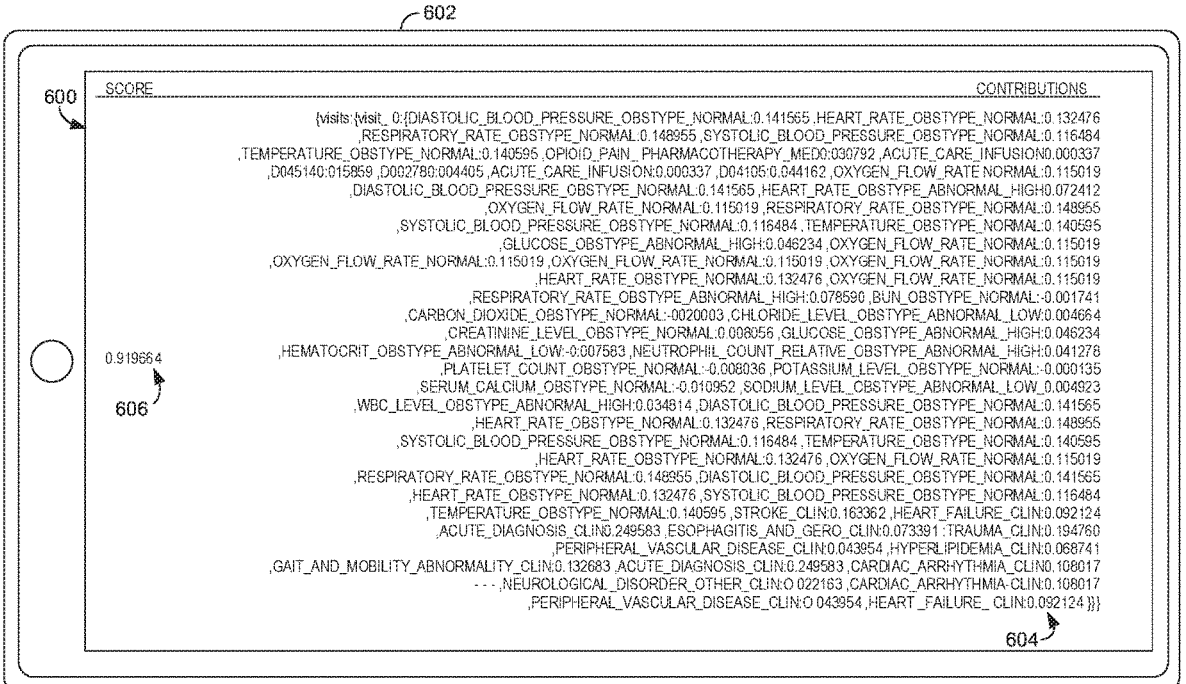
FIG. 6 depicts a graphical user interface providing contribution scores of patient data that may be utilized for predicting readmission for a post-acute care patient, in accordance with an embodiment of the disclosure.

FIG. 6 depicts an example screenshot from a computing device, which aspects of an example graphical user interface (GUI) 600 for a computer software application or app. The GUI 600 depicted in the screenshot in FIG. 6 may be for a computer decision support application, such as decision support application 140 described in conjunction with FIG. 1A. The computer decision support applications of the GUI 600 may be operating on (and GUI 600 may be displayed on) a user computer device 602, which may be embodied as computer system 120 in FIG. 1. Specifically, GUI 600 identifies a readmission score 606 for a patient and contribution scores 604 for patient data used to determine the readmission score 606. GUI 600 provides readmission score 606 and contribution scores 604 in JSON format, which may be output from a service, such as an example embodiment of computation service 126 in FIG. 1A (which may be a web service), running the machine learning model, such as an RNN, to predict readmission. In some embodiment, the prediction scores and/or contribution scores displayed in JSON format in FIG. 6 may be utilized to generate one or more other GUIs disclosed herein, such as GUIs 400, 430, and/or 500. Additional details regarding generating a readmission prediction and the contribution values are discussed with respect to method 200 of FIG. 2.

Figure 7:
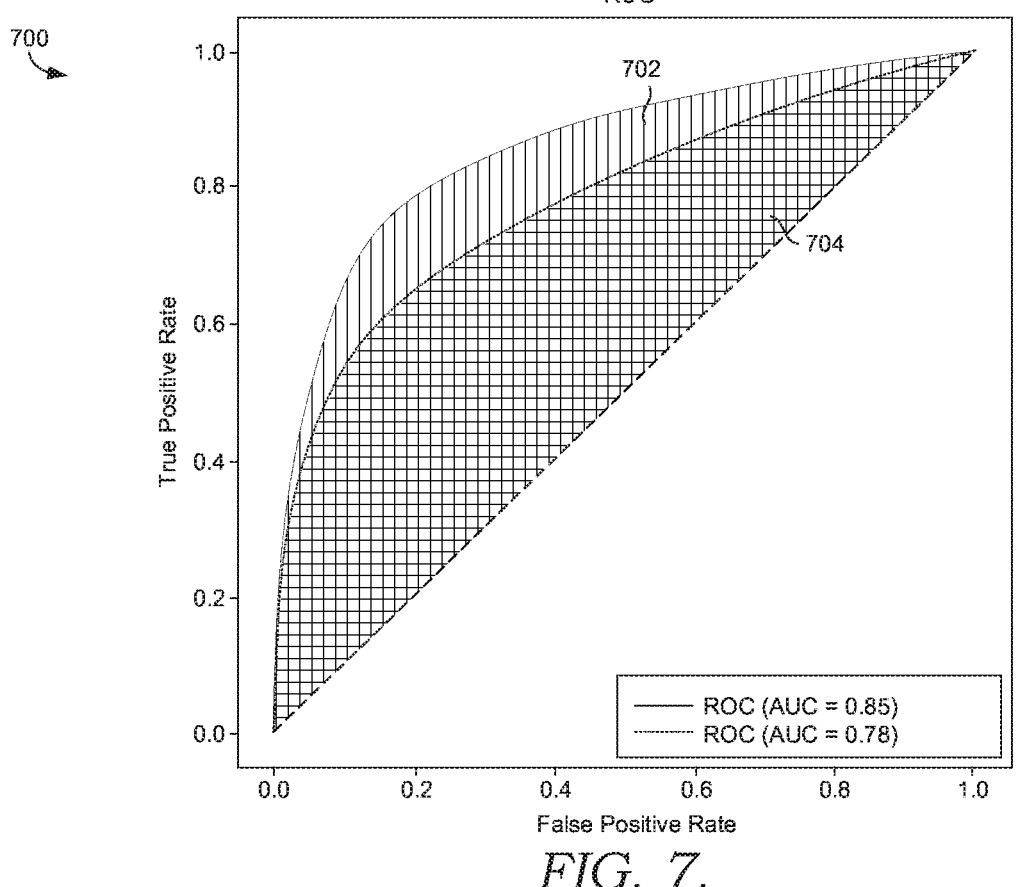
FIG. 7 depicts a representation of statistical performance of an example readmission predictor, in accordance with embodiments of the disclosure.

Turning to FIG. 7, performance of an embodiment of the disclosed readmission predictor that was actually reduced to practice is illustrated. In an embodiment reduced to practice, reference patient data was used to train a recurrent neural network using data from multiple sources. One data source including data for patients receiving post-acute care services in inpatient rehabilitation facilities, and a second data source included data for patients receiving post-acute care in home health services. The inpatient rehabilitation facility data included 284,682 encounters, 20,167 unique diagnoses codes, 9,259 unique medication codes, and 803 unique lab results codes from a two-year time period. The home health data includes 26,281 unique encounters within the same two-year period and included questionnaire data with 358 unique questions. Additionally, in this embodiment, health facility data was used, including billing and diagnoses codes. The data was divided into 70% used for training, 10% used for validation, and 20% used for testing.

In this embodiment actually reduced to practice, positive precision (PPV), positive recall (sensitivity), and a positive F1-score were calculated as measurements of performance. Positive precision was 0.6; positive recall was 0.72; and positive F1-scores was 0.65. When using the same data on a conventional model, positive precision was 0.32, positive recall was 0.65, and positive F1-score was 0.43. As such, the disclosed predictor showed an improvement on the conventional tools in precision, recall, and F1-score.

Further, the receiver operating characteristic ("ROC") graph 700 in FIG. 7 illustrates the improved performance of the embodiment actually reduced to practice. FIG. 7 includes a curve and resulting AUC 704 (measuring approximately 0.77) from using an existing for predicting readmission for post-acute care patients. FIG. 7 also includes a curve and resulting AUC 702 (measuring approximately 0.85) from using an embodiment of the present disclosure in which a recurrent neural network is utilized for predicting readmission. As such, FIG. 7 illustrates that embodiments of the present disclosure provide more accurate predictions than existing tools.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A non-transitory computer storage media having computer-executable instructions embodied thereon that, when executed, provide a method for predicting readmission for a patient, the method comprising:

training a recurrent neural network based on patient event data, of a plurality of patients, to predict readmission probabilities for patients discharged from acute care facilities and having received post-acute care services, the patient event data of the plurality of patients comprising (a) healthcare visits, (b) healthcare events, and (c) patient readmission data;

receiving patient data for a patient (i) discharged from an acute care facility and (ii) currently receiving post-acute care services, the patient data corresponding to patient care services received over time;

generating at least two sequences based on the patient data, wherein the at least two sequences comprise:

(a) a visits sequence indicating a plurality of healthcare visits by the patient, wherein the visits sequence is in reverse chronological order, and (b) an events sequence indicating a plurality of healthcare events for the patient, wherein the events sequence is in chronological order;

applying the recurrent neural network to a combination of time series data corresponding to the at least two sequences to predict a probability of the patient being readmitted into the acute care facility within a future time interval, wherein the recurrent neural network comprises a visits layer that receives the visits sequence and an events layer that receives the events sequence;

wherein prior to discharge of the patient from receiving the post-acute care services, an action for treatment of the patient is initiated based on the probability of the patient being readmitted into the acute care facility; and retraining the recurrent neural network based on feedback corresponding to the probability of the patient being readmitted into the acute care facility.

2. The non-transitory computer storage media of claim 1, wherein the action for the treatment comprises one or more of modifying discharge instructions for the patient or scheduling a follow-up appointment for the patient.

3. The non-transitory computer storage media of claim 1, wherein at least one of the events sequence and the visits sequence comprises feature values, wherein the feature values are determined using a default reference range for a larger population.

4. The non-transitory computer storage media of claim 1, wherein the events sequence comprises feature values for one or more of a lab result, a diagnosis, a medication, and a procedure for the patient.

5. The non-transitory computer storage media of claim 1, wherein at least one of the events sequence and the visits sequence comprises feature values, wherein the feature values are determined using a reference range specific to the patient.

6. The non-transitory computer storage media of claim 5, wherein the reference range specific to the patient includes normal values and abnormal values.

7. The non-transitory computer storage media of claim 1, wherein the patient event data is for patients currently receiving post-acute care services and patients that have previously received post-acute care services.

8. The non-transitory computer storage media of claim 1, wherein the action for the treatment comprises one or more of, ordering additional testing or prescribing medications designed to reduce the probability of readmission, for the patient.

9. The non-transitory computer storage media of claim 1, wherein the events layer and the visits layer are gated recurrent unit layers.

10. A computerized method for implementing a decision support tool for a patient receiving post-acute care services, the computerized method comprising:

training a recurrent neural network based on patient event data, of a plurality of patients, to predict readmission probabilities for patients discharged from acute care facilities and having received post-acute care, the patient event data of the plurality of patients comprising (a) healthcare visits, (b) healthcare events, and (c) patient readmission data;

receiving patient data for a patient (i) discharged from an acute care facility and (ii) currently receiving post-acute care, the patient data corresponding to patient care services received over time;

generating at least two sequences based on the patient data, wherein the at least two sequences comprise:

(a) a visits sequence indicating a plurality of healthcare visits by the patient, wherein the visits sequence is in reverse chronological order, and (b) an events sequence indicating a plurality of healthcare events for the patient, wherein the events sequence is in chronological order;

applying the recurrent neural network to a combination of time series data corresponding to the at least two sequences to predict a probability of the patient being readmitted into the acute care facility within a future time interval, wherein the recurrent neural network comprises a visits layer that receives the visits sequence and an events layer that receives the events sequence;

wherein prior to discharge of the patient from receiving post-acute care services, an action for treatment of the patient is initiated based on the probability of the patient being readmitted into the acute care facility; and retraining the recurrent neural network based on feedback corresponding to the probability of the patient being readmitted into the acute care facility.

11. The computerized method of claim 10, further comprising converting the patient data that is in at least one nomenclature into a standard nomenclature using an ontology.

12. The computerized method of claim 10, wherein the action for the treatment comprises displaying the readmission probability and providing an alert when the readmission probability is above a threshold.

13. The computerized method of claim 10, wherein the action for the treatment comprises scheduling a visit for the patient with a healthcare provider.

14. The computerized method of claim 13, further comprising:

determining a contribution score for at least some features within the patient data utilized to determine the readmission probability for the patient; and providing the contribution score for display.

15. The computerized method of claim 10, wherein the healthcare events comprise a diagnosis, a medication, or a procedure.

16. The computerized method of claim 10, wherein the future time interval comprises 90 days and the readmission probability is determined three days prior to a scheduled discharge of the patient from receiving the post-acute care services.

17. A computerized system for predicting a probability of being readmitted for a patient who has received post-acute care services, the system comprising:

one or more processors; and one or more computer storage media storing computer-useable instructions that, when used by the one or more processors, cause the one or more processors to perform a method, the method comprising:

training a recurrent neural network based on patient event data of a plurality of patients to predict readmission probabilities for patients discharged from acute care facilities and having received post-acute care services, the patient event data of the plurality of patients comprising (a) healthcare visits, (b) healthcare events, and (c) patient readmission data;

receiving patient data for a patient (i) discharged from an acute care facility and (ii) currently receiving post-acute care services;

generating at least two sequences based on the patient data, wherein the at least two sequences comprise:

(a) a visits sequence indicating a plurality of healthcare visits by the patient, wherein the visits sequence is in reverse chronological order, and (b) an events sequence indicating a plurality of healthcare events for the patient, wherein the events sequence is in chronological order;

applying the recurrent neural network to a combination of time series data corresponding to the at least two sequences to predict a probability of the patient being readmitted, into the acute care facility within a future time interval, wherein the recurrent neural network comprises a visits layer that receives the visits sequence and an events layer that receives the events sequence;

wherein prior to discharge of the patient from receiving post-acute care services, an action for treatment of the patient is initiated based on the probability of the patient being readmitted into the acute care facility; and retraining the recurrent neural network based on feedback corresponding to the probability of the patient being readmitted into the acute care facility.

18. The computerized system of claim 17, wherein the visits sequence is based on at least two patient visits, wherein at least one of the at least two patient visits includes services other than the post-acute care services.

19. The computerized system of claim 17, wherein the healthcare events of the events sequence comprise a diagnosis, a medication, or a procedure, wherein the visits sequence is arranged in reverse chronological order.

20. The computerized system of claim 17, wherein the future time interval comprises 90 days.

21. The computerized system of claim 17, wherein the action comprises displaying the probability of the patient being readmitted and providing an alert to a healthcare provider when the probability of the patient being readmitted is above a threshold.

* * * * *